United States Patent [19]

Richardson

[11] Patent Number: 4,992,454

[45] Date of Patent: Feb. 12, 1991

[54] ANTIFUNGAL 1,3-BIS (1H-1,2,4-TRIAZOL-1-YL)-2-ARYL BUTAN-2-OLS AND DERIVATIVES THEREOF

[75] Inventor: Kenneth Richardson, Canterbury, England

[73] Assignee: Pfizer Inc., New York, N.Y.

[21] Appl. No.: 584,216

[22] Filed: Feb. 27, 1984

[30] Foreign Application Priority Data

Mar. 16, 1983 [GB] United Kingdom ............... 8307232
Nov. 25, 1983 [GB] United Kingdom ............... 8331475

[51] Int. Cl.$^5$ ............... A01N 43/40; A01N 43/653; C07D 401/14; C07D 249/08
[52] U.S. Cl. ............... 514/340; 514/383; 546/276; 548/266.6
[58] Field of Search ............... 548/262, 266.6; 546/276; 424/269, 263; 514/383, 340

[56] References Cited

U.S. PATENT DOCUMENTS 4,404,216  9/1983  Richardson ............... 548/262
4,510,148  4/1985  Richardson et al. ............... 514/340

FOREIGN PATENT DOCUMENTS 0044605  1/1982  European Pat. Off. ............ 548/262
0120276  10/1984  European Pat. Off. ............ 548/262
0122693  10/1984  European Pat. Off. ............ 548/262

Primary Examiner—Richard L. Raymond
Assistant Examiner—Patricia L. Morris
Attorney, Agent, or Firm—Peter C. Richardson; J. Trevor Lumb

[57] ABSTRACT

Triazole antifungal agents of the formula

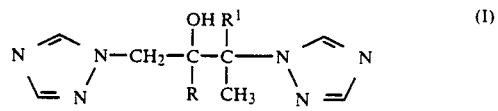

where R is 5-chloropyrid-2-yl or phenyl optionally substituted by 1 to 3 substituents each independently selected from F, Cl, Br, I, $CF_3$, $C_1$–$C_4$ alkyl and $C_1$–$C_4$ alkoxy; and $R^1$ is H or $CH_3$; and their O-esters, O-ethers and pharmaceutically and agriculturally acceptable salts. The compounds are useful as human and agricultural antifungal agents.

2 Claims, No Drawings

ANTIFUNGAL 1,3-BIS (1H-1,2,4-TRIAZOL-1-YL)-2-ARYL BUTAN-2-OLS AND DERIVATIVES THEREOF

BACKGROUND OF THE INVENTION

This invention relates to novel bis-triazole derivatives which have antifungal activity and are useful in the treatment of fungal infections in animals, including humans, and as agricultural fungicides.

British patent application No. 2,078,719A, published Jan. 13, 1982 and European patent application No. 44,605, published Jan. 27, 1982 (both assigned to Imperial Chemical Industries Limited) disclose compounds of the general formula:

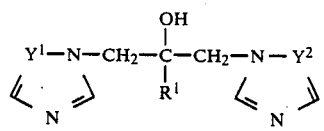

where $R^1$ is an optionally-substituted alkyl, cycloalkyl (e.g., cyclopentyl or cyclohexyl), aryl (e.g., phenyl or 2,4-dichloro-phenyl) or aralkyl (e.g., benzyl) group, and $Y^1$ and $Y^2$ are =CH or =N—; and salts or metal complexes and ethers or esters thereof. These compounds are stated to be useful as fungicides and as plant growth regulants. They are also stated to be active against the fungus diseases of humans. Among the compounds specifically disclosed therein are such bis-triazole derivatives as 2-(2,4-dichlorophenyl)-1,3-bis(1H-1,2,4-triazol-1-yl)propan-2-ol and its corresponding 2- and 4-chlorophenyl analogs. The corresponding 3-chlorophenyl and 4-bromophenyl compounds are also embraced by the statement of invention. However, these particular compounds have now been found to be teratogenic, which severely limits their use in treating human mycoses.

U.S. Pat. No. 4,404,216, issued Sept. 13, 1983 is directed to the single antifungal compound 2-(2,4-difluorophenyl)-1,3-bis(1H-1,2,4-triazol-yl)propan-2-ol, a compound having the above formula but wherein $R^1$ is 2,4-difluorophenyl.

SUMMARY OF THE INVENTION

According to the invention, there are provided compounds of the formula:

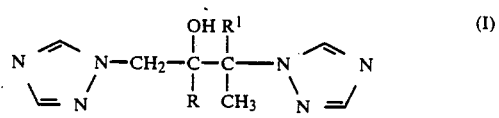

where R is 5-chloropyrid-2-yl or phenyl optionally substituted by 1 to 3 substituents each independently selected from F, Cl, Br, I, $CF_3$, $C_1$-$C_4$ alkyl and $C_1$-$C_4$ alkoxy; and $R^1$ is H or $CH_3$; and their O-esters, O-ethers and pharmaceutically and agriculturally acceptable salts.

$C_3$ and $C_4$ alkyl and alkoxy groups can be straight or branched chain.

The invention also provides a pharmaceutical composition comprising a compound of the formula (I) or an O-ester, O-ether or pharmaceutically acceptable salt thereof, together with a pharmaceutically acceptable diluent or carrier.

The invention further provides a compound of the formula (I) or an O-ester, O-ether or pharmaceutically acceptable salt thereof, for use in medicine, in particular for treating fungal infections in animals, including humans.

The invention yet further provides an antifungal composition for agricultural (including horticultural) use, comprising a compound of the formula (I) or an O-ester, O-ether or agriculturally acceptable salt thereof, together with an agriculturally acceptable diluent or carrier.

The invention yet further provides a method of treating an animal (including a human being), plant or seed having a fungal infection, which comprises treating said animal, plant or seed, or the locus of said plant, with an effective amount of a compound of the formula (I) or O-ester or O-ether thereof or with, as appropriate, a pharmaceutically or agriculturally acceptable salt thereof.

When R is said optionally substituted phenyl group, it is preferably phenyl substituted by 1 to 3 substituents, more preferably 1 or 2 substituents, each independently selected from F, Cl, Br, I and $CF_3$. The preferred individual groups represented by R are 4-fluorophenyl, 4-chlorophenyl, 4-bromophenyl, 4-iodophenyl, 4-trifluoromethylphenyl, 2-chlorophenyl, 2,4-dichlorophenyl, 2,4-difluorophenyl, 2-chloro-4-fluorophenyl, 2-fluoro-4-chlorophenyl, 2,5-difluorophenyl, 2,4,6-trifluorophenyl, 4-bromo-2,5-difluorophenyl and 5-chloro-pyrid-2-yl. The most preferred groups represented by R are 2,4-difluorophenyl, 2,4-dichlorophenyl, 4-fluorophenyl, 4-chlorophenyl and 5-chloro-pyrid-2-yl.

In the most preferred individual compound, $R^1$ is $CH_3$ and R is 4-chlorophenyl.

Typical O-esters are $C_2$-$C_4$ alkanoyl (e.g. acetyl) and benzoyl esters. The phenyl ring of benzoyl esters can be substituted by, for example, 1 or 2 $C_1$-$C_4$ alkyl or halo groups. Typical O-ethers are $C_1$-$C_4$ alkyl, $C_2$-$C_4$ alkenyl, phenyl-($C_1$-$C_4$ alkyl) and phenyl ethers. Again said phenyl groups can be ring substituted by, e.g., 1 or 2 $C_2$-$C_4$ alkyl or halo groups.

DETAILED DESCRIPTION OF THE INVENTION

The compounds of the formula (I) can be prepared in conventional manner according to the following reaction scheme:

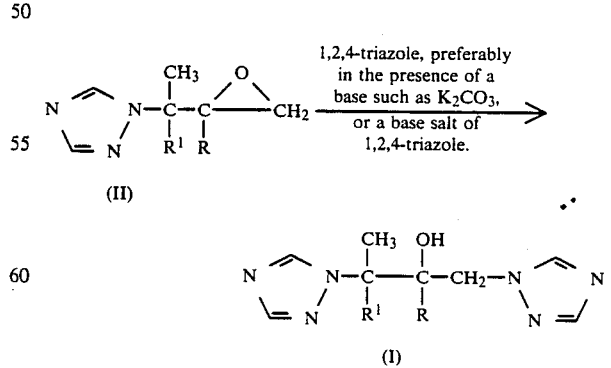

In a typical reaction, the epoxide (II), 1,2,4-triazole and anhydrous potassium carbonate are heated together at, say, 40°–120° C., in a suitable solvent, e.g. anhydrous dimethylformamide, until the reaction is complete, usually in 2-16 hours. The product (I) can then be isolated and purified in a conventional manner.

If a base salt of 1,2,4-triazole is used, it is preferably an alkali metal salt.

The starting materials of the formula (II) are obtainable conventionally, e.g.:

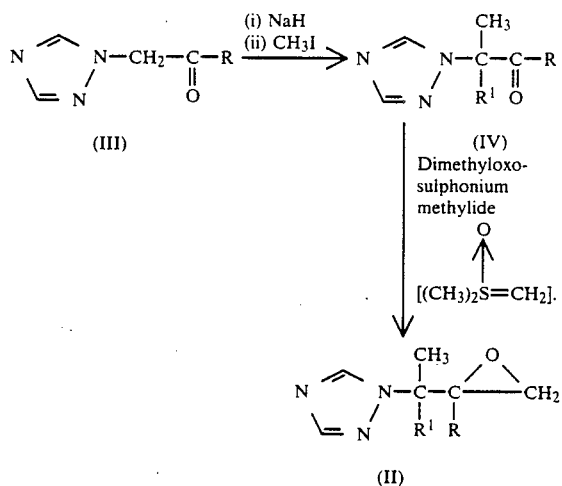

In the first stage of the above scheme, about one equivalent of sodium hydride and about one equivalent of methyl iodide should be used when monomethylation is desired, and at least two equivalents of each when dimethylation is required.

Trimethylsulphoxonium iodide and either sodium hydride or sodium hydroxide/cetrimide can be used to generate dimethyloxosulphonium methylide in situ. When R is a phenyl group containing no ortho substituent, the cetrimide/NaOH route should be used.

The ketones (III) are either known compounds (see e.g. European patent application publication No. 0044605 or U.K. patent application publication No. 2099818A) or can be prepared by methods analogous to those of the prior art.

According to a further aspect of the invention there is provided a process for preparing the compounds of the formula (I) in which $R^1$ is H, which comprises reacting a compound of the formula:

$$\underset{\underset{R}{|}\phantom{xx}\underset{CH_3}{|}}{X-CH_2-\overset{OH}{\underset{|}{C}}-CH-X^1} \quad (V)$$

where X and $X^1$ are each a leaving group, preferably Cl, Br, or I, and R is as defined for formula (I), with either 1,2,4-triazole, preferably in the presence of a base, e.g. potassium carbonate, or with a base salt, preferably an alkali metal salt, of 1,2,4-triazole.

Preferably X and $X^1$ are the same and are most preferably Br.

Typically the compound (V), 1,2,4-triazole and potassium carbonate are heated together at, say, 40°-120° C., in a suitable organic solvent, e.g. dimethylformamide, until the reaction is complete. The product can be isolated and purified conventionally.

The starting materials (V) are obtainable conventionally, e.g.:

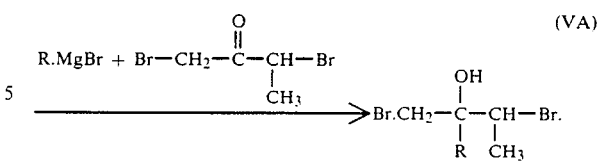

It is not necessary to isolate the intermediate (V). It can be used directly.

The O-esters and O-ethers can be prepared conventionally, typically by reacting an alkali metal salt of compound (I) with the appropriate chloro- or bromo-compound, e.g. an alkanoyl or benzoyl chloride, or alkyl, alkenyl, benzyl or phenyl chloride or bromide.

Pharmaceutically acceptable acid addition salts of the compounds of the formula (I) are those formed from strong acids which form non-toxic acid addition salts, such as hydrochloric, hydrobromic, sulphuric, oxalic and methanesulphonic acids.

The salts may be obtained by conventional procedures, e.g. by mixing solutions containing approximately equimolar amounts of the free base and desired acid, and the required salt is collected by filtration, if insoluble, or by evaporation of the solvent.

The compounds of the present application have been found to possess unexpectedly good activity against infections caused by the clinically-important Aspergillus fungi.

The compounds of the formula (I) and their O-esters, O-ethers and salts are antifungal agents, useful in combating fungal infections in animals, including humans. For example they are useful in treating topical fungal infections in man caused by, among other organisms, species of Candida, Trichophyton, Microsporum or Epidermophyton, or in mucosal infections caused by Candida albicans (e.g. thrush and vaginal candidiasis). They can also be used in the treatment of systemic fungal infections caused by, for example, Candida albicans, Cryptococcus neoformans, Aspergillus flavus, Aspergillus fumigatus, Coccidioides, Paracoccidioides, Histoplasma or Blastomyces.

The in vitro evaluation of the antifungal activity of the compounds can be performed by determining the minimum inhibitory concentration (m.i.c.) of the test compounds in a suitable medium at which growth of the particular micro-organism fails to occur. In practice, a series of agar plates, each having the test compound incorporated at a particular concentration is inoculated with a standard culture of, for example, Candida albicans and each plate is then incubated for 48 hours at 37° C. The plates are then examined for the presence or absence of growth of the fungus and the appropriate m.i.c. value is noted. Other micro-organisms used in such tests can include Candida albicans, Aspergillus fumigatus, Trichophyton spp; Microsporum spp; Epidermophyton floccosum, Coccidioides immitis and Torulopsis glabrata.

The in vivo evaluation of the compounds can be carried out at a series of dose levels by intraperitoneal or intravenous injection or by oral administration, to mice which are inoculated with, e.g., a strain of Candida albicans or Aspergillus flavus. Activity is based on the survival of a treated group of mice after the death of an untreated group of mice. The dose level at which the compound provides 50% protection against the lethal effect of the infection ($PD_{50}$) is noted.

For human use, the antifungal compounds of the formula (I) and their salts, O-ethers and O-esters can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs or suspensions containing flavouring or colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the antifungal compounds of the formula (I) and their salts, O-ethers and O-esters will be from 0.1 to 10 mg/kg (in divided doses) when administered by either the oral or parenteral route. Thus tablets or capsules of the compounds will contain from 5 mg to 0.5 g of active compound for administration singly or two or more at a time as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the antifungal compounds of formula (I) can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

The compounds of the formula (I) and their O-ethers, O-esters and salts also have activity against a variety of plant pathogenic fungi, including for example various rusts, mildews and moulds, and the compounds are thus useful for treating plants and seeds to eradicate or prevent such diseases.

The in vitro evaluation of the activity of the compounds against plant fungi can be determined by measuring their minimum inhibitory concentrations in the same way as previously described except that the plates are incubated at 30° C. for 48 hours or longer before being examined for the presence or absence of growth.

Micro-organisms used in such tests include *Cochliobolus carbonum, Pyricularia oryzae, Glomerella cingulata, Penicillium digitatum, Botrytis cinerea* and *Rhizoctonia solani*.

For agricultural and horticultural purposes the compounds and their agriculturally acceptable salts are preferably used in the form of a composition formulated as appropriate to the particular use and purpose desired. Thus the compounds may be applied in the form of dusting powders, or granules, seed dressings, aqueous solutions, dispersions or emulsions, dips, sprays, aerosols or smokes. Compositions may also be supplied in the form of dispersible powders, granules or grains, or concentrates for dilution prior to use. Such compositions may contain such conventional carriers, diluents or adjuvants as are known and acceptable in agriculture and horticulture and they are manufactured in accordance with conventional procedures. The compositions may also incorporate other active ingredients, for example, compounds having herbicidal or insecticidal activity or a further fungicide. The compounds and compositions can be applied in a number of ways, for example they can be applied directly to the plant foliage, stems, branches, seeds or roots or to the soil or other growing medium, and they may be used not only to eradicate disease, but also prophylactically to protect the plants or seeds from attack.

The following Examples illustrate the invention. All temperatures are in °C.

EXAMPLE 1

1,3-Bis(1H-1,2,4-triazol-1-yl)-2-(2,4-difluorophenyl)-3-methyl-butan-2-ol

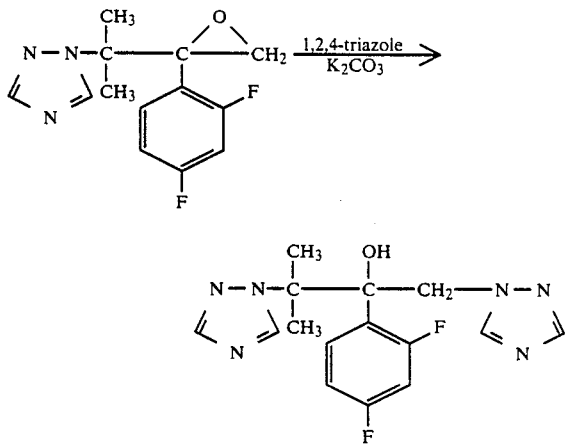

To a solution of 2-(2,4-difluorophenyl)-2-[2-(1H-1,2,4-triazol-1-yl)prop-2-yl]oxirane (0.49 g, 1.8 m.Mole) in dimethylformamide (20 ml) was added 1,2,4-triazole (0.25 g, 3.6 m.Mole) and anhydrous potassium carbonate (0.25 g, 1.8 m.Mole). Heating at 80°, with stirring, was carried out for four hours. The solvent was then evaporated, water (100 ml.) was added, and the mixture was extracted with methylene chloride (3×30 ml). The combined organic extracts were washed with water (3×20 ml), dried over anhydrous magnesium sulphate and evaporated to an impure solid, weight 0.73 g.

Purification was carried out using a flash column of Merck "Keiselgel 60" (Trademark) 230–400 mesh silica, eluting with methylene chloride containing gradually increasing amounts of methanol (from 1 to 5%). The appropriate fractions, on evaporation, gave an oil which was crystallised from diisopropylether giving the title compound 0.36 g, m.p. 155°–157° (60% yield).

Analysis %: Calculated for $C_{15}H_{16}F_2N_6O$: C,53.9; H,4.8; N,25.1. Found: C,53.6; H,4.8; N,24.9.

N.m.r. and mass spectrometry data for the product were consistent with the stated structure.

EXAMPLE 2

1,3-Bis(1H-1,2,4-triazol-1-yl)-2-(2,4-difluorophenyl)-butan-2-ol

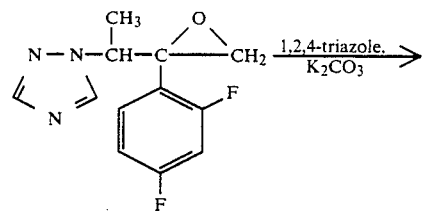

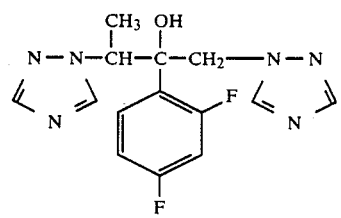

To a solution of 2-(2,4-difluorophenyl)-2-[1-(1H-1,2,4-triazol-1-yl)ethyl]oxirane (0.5 g, 1.9 m.Mole) in dimethylformamide (20 ml) was added 1,2,4-triazole (0.27 g, 3.8 m.Mole) and anhydrous potassium carbonate (0.27 g, 1.9 m.Mole). Heating, with stirring, was carried out for three hours at 85°. The solvent was evaporated, water (100 ml.) was added and the mixture was then extracted with methylene chloride (3×30 ml). The combined organic extracts were washed with water (3×20 ml), dried over anhydrous magnesium sulphate, and evaporated to an impure solid, weight 0.6 g.

Purification cas carried out using a flash column of Merck "Keiselgel 60" 230-400 mesh silica, eluting with methylene chloride containing gradually increasing amount of methanol (from 1 to 5%). The appropriate fractions, on evaporation, gave a solid which was recrystallised from isopropanol giving the pure title compound, 0.42 g, m.p. 186°-188° (60% yield).

Analysis %: Calculated for $C_{14}H_{14}F_2N_6O$: C,52.5, H,4.4, N,26.2. Found: C,52.4; H,4.5, N,26.5.

N.m.r., i.r. and mass spectrometry data for the product were consistent with the stated structure.

EXAMPLE 3

1,3-Bis(1H-1,2,4-triazol-1-yl)-2-(5-chloropyrid-2-yl)butan-2-ol

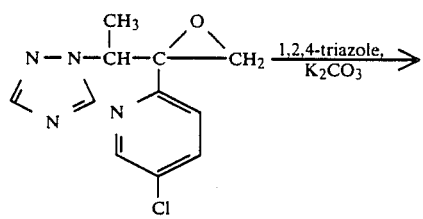

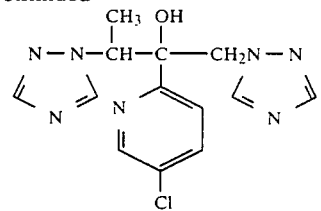

To a solution of 2-[5-chloropyrid-2-yl]-2-[1-(1H-1,2,4-triazol-1-yl)ethyl]oxirane (70 mg; 0.28 m.Mole) in dimethylformamide (5 ml) was added 1,2,4-triazole (39 mg; 0.56 m.Mole) and anhydrous potassium carbonate (39 mg; 0.28 m.Mole). Heating, with stirring, was carried out for three hours at 80°. The solvent was then evaporated, water (20 ml.) was added, and the mixture was extracted with methylene chloride (3×10 ml). The combined organic extracts were washed with water (3×5 ml), dried over anhydrous magnesium sulphate, and evaporated to an oil (100 mg). Purification was carried out using a flash column of Merck "Kieselgel 60" 230-400 mesh silica, eluting with methylene chloride containing gradually increasing amounts of methanol (from 1 to 5%). The appropriate fractions, on evaporation, gave the pure title compound, 25 mg; m.p. 156°-157° (28.1% yield).

N.m.r. and i.r. data for the product were consistent with stated structure.

EXAMPLE 4

1,3-Bis-(1H-1,2,4-triazol-1-yl)-2-(4-chlorophenyl)-3-methylbutan-2-ol

4'-Chloro-2-methyl-2-(1H-1,2,4-triazol-1-yl)propiophenone

4'-Chloro-2-(1H-1,2,4-triazol-1-yl)propiophenone (2 g.) in dry tetrahydrofuran (30 ml) was added to a suspension of sodium hydride (480 mg. of a 60% dispersion in oil) in dry tetrahydrofuran (20 ml) at 0° under a nitrogen atmosphere. After stirring for 10 minutes, methyl iodide (2.28 g.) in dry tetrahydrofuran (10 ml.) was added dropwise and the reaction mixture was then stirred at 0° for 1 hour and then at room temperature overnight. The reaction mixture was then diluted with water (20 ml), extracted with ether (3×25 ml), and the combined organic extracts were washed with water and dried (MgSO₄). The residue obtained after removal of the solvent was flash chromatographed on silica (150 g.) using ethyl acetate/hexane/diethylamine (50:50:3 v/v/v) for elution and the product-containing fractions on evaporation followed by crystallisation of the residue from ethyl acetate/hexane furnished the title compound, (1.68 g., 84% yield), m.p. 118°-9°.

Analysis %: Found: C,57.8; H,4.9; N,16.9. Calculated for $C_{12}H_{12}ClN_3O$: C,57.7; H,4.8; N,16.8.

The starting 4'-chloro-2-(1H-1,2,4-triazol-1-yl)propiophenone was prepared according to Preparation 6.

(B) 2-(4-Chlorophenyl)-2-[2-(1H-1,2,4-triazol-1-yl)-prop-2-yl]oxirane

A mixture of 4'-chloro-2-methyl-2-(1H-1,2,4-triazol-1-yl)propiophenone (1.375 g), trimethyl sulphoxonium iodide (1.6 g), aqueous sodium hydroxide (5N; 13.5 ml.), cetrimide (80 mg.) and 1,1,1-trichloroethane (30 ml.) was heated at 80° for 24 hours. The solution was cooled and diluted with methylene chloride (30 ml.), and the organic layer was separated and dried (MgSO₄). Removal of the solvent, followed by flash chromatography of the residue on silica (100 g.) using ethyl acetate/hexane/diethylamine (40:60:3 v/v/v) for elution, gave, after collection of appropriate fractions and evaporation, the title oxirane as an oil in 79% yield, 1.15 g.

Mass spec.: Found parent ion m/e 263, (M+). Calculated for $C_{13}H_{14}ClN_3O$: 263 (M+).

(C) 1,3-Bis(1H-1,2,4-triazol-1-yl)-2-(4-chlorophenyl)-3-methylbutan-2-ol

A mixture of 2-(4-chlorophenyl)-2-[2-(1H-1,2,4-triazol-1-yl)prop-2-yl]oxirane (1.1 g.), 1,2,4-triazole (2 g.), potassium carbonate (5 g.) and dry dimethylformamide (25 ml.) was heated at 80° under a nitrogen atmosphere for 16 hours. The reaction mixture was then cooled, filtered, washed with xylene and the filtrate was evaporated in vacuo. The residue was azeotroped with xylene (2×30 ml.) and then partitioned between methylene chloride (50 ml.) and water (50 ml.). The aqueous phase was extracted with methylene chloride (3×50 ml), and the combined organic phases were washed with water (50 ml.), and dried (MgSO4). The residue obtained after removal of the solvent was flash chromatographed on silica (150 g) using methylene chloride/methanol/saturated aqueous ammonia (93:7:1 v/v/v), for elution. The product-containing fractions on evaporation followed by crystallisation from ethyl acetate/hexane yielded 983 mg. (71% yield) of the title compound, m.p. 128°-9°.

Analysis %: Found: C,54.1; H,5.2; N,25.4; Calculated for $C_{15}H_{17}ClN_6O$: C,54.1; H,5.1; N,25.3.

EXAMPLE 5

Preparation of
1,3-Bis-(1H-1,2,4-triazol-1-yl)-2-(4-chlorophenyl)butan-2-ol

Route (a)

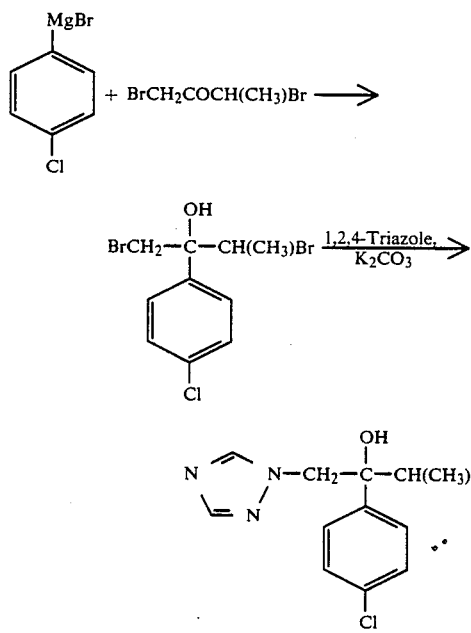

4-Chlorophenyl magnesium bromide in ether (80 ml) [prepared from 4-chlorobromobenzene (15.2 g) and magnesium turnings (2.8 g)]was added under a nitrogen atmosphere over 30 minutes by a double ended needle to a solution of 1,3-dibromobutan-2-one (9.2 g) (Org. Synthesis, 53, 123) in dry ether (50 ml) at −78°. After stirring at −78° for 1 hour, the resulting mixture was quenched with saturated ammonium chloride solution and allowed to attain room temperature. The ether layer was separated, the aqueous layer extracted with ether (3×20 ml), and the combined ether extracts were washed with brine and dried (MgSO4). The residue obtained after removal of the ether was added to a mixture of 1,2,4-triazole (8 g), potassium carbonate (20 g) and dimethylformamide (50 ml) under a nitrogen atmosphere and the mixture was heated at 70° overnight. The cooled solution was filtered, the solid was washed with xylene (50 ml) and the combined filtrates were evaporated in vacuo. The last traces of dimethylformamide were removed by azeotroping with xylene (2×30 ml). The crude residue was partitioned between methylene chloride (200 ml) and water (100 ml), and the methylene chloride extract was washed with water and dried (MgSO4). After removal of the methylene chloride in vacuo, the residue was flash chromatographed on silica (150 g), using methylene chloride containing 8% (by volume) methanol for elution. Appropriate fractions (i.e. fractions 29-39, each of 50 ml) were combined and, on evaporation, furnished 1.1 g of a mixture of diastereomeric pairs. The isomeric pairs were separated by flash chromatography on silica (100 g) by eluting with ethyl acetate:diethylamine:methanol (80:20:2 by volume). Fractions 13-16 (each of 25 ml) were combined and evaporated to yield isomeric pair 1, (114 mg), m.p. 112°-113° from ethyl acetate/hexane. (Mass spectral data m/e 318 (M+); calculated for $C_{14}H_{15}ClN_6O$: M+=318). Evaporation of fractions 31-49 (again each of 25 ml) followed by crystallisation from ethyl acetate/hexane yielded isomeric pair 2 (246 mg), m.p. 50°-51° (Mass spectral data m/e 318(M+); calculated for $C_{14}H_{15}ClN_6O$: M+=318).

Isomeric Pair 1

N.M.R. (CDCl3). δ=1.25 (d,J=7 Hz,3H,CH3), 3.76 (d,J=13 Hz,1H,N—CH2), 4.32 (d,J=13 Hz, 1H,N—CH2), 4.92(q,J=7 Hz,1H,N—CH[CH3]) 5.48 (s,—OH: exchangeable with D2O), 7.12 (m,4H,C6H4), [7.55 (s,1H), 7.70 (s,1H), 7.92 (s,1H), 8.30 (s,1H)-triazole protons].

Isomeric Pair 2

N.M.R. (CDCl3). δ=1.53 (d,J=7 Hz,3H,CH3), 4.56 (s,2H,N—CH2), 4.72 (J=7 Hz, 1H, $$\overset{CH_3}{\underset{|}{CH}},$$

5.52 (s,OH: exchangeable with D2O), 6.95 (m,4H,C6H4), [7.65 (s,1H), 7.78 (s,2H) 7.88 (s,1H)-triazole protons].

Route (b)

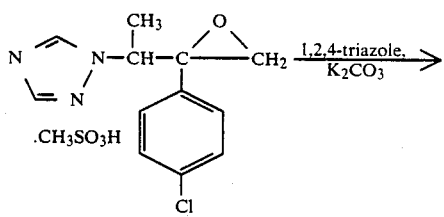

-continued

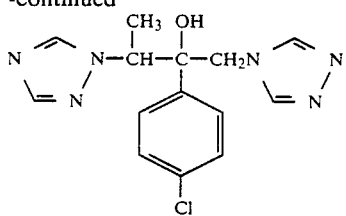

Reaction of 2-(4-chlorophenyl)-2-[1-(1H-1,2,4-triazol-1-yl) ethyl]oxirane methanesulphonate salt (1.82 g) with 1,2,4-triazole (2 g) and potassium carbonate (3.4 g) in dimethylformamide (30 ml) under similar reaction conditions to route (a) also with extraction and isolation procedures similar to route (a), yielded the said isomeric pair 1 (796 mg., m.p. 112°–113°) and isomeric pair 2 (70 mg., m.p. 50°–52°) characterised spectroscopically to be the same as the products of Route (a).

EXAMPLE 6

1,3-Bis(1H-1,2,4-triazol-1-yl)-2-(2,4-difluorophenyl)-butan-2-ol was prepared and separated into its two diastereomeric pairs using a procedure similar to that of route (a) of the previous Example using, of course, appropriate starting materials. Isomeric pair 1 was characterised and found to be identical to the product of Example 2. Isomeric pair 2 had an m.p. of 123°–5° and had a microanalysis as follows:

Analysis %: Found: C,52.55; H,4.5; N,26.1. Calculated for $C_{14}H_{14}F_2N_6O$: C,52.5: H,4.4; N,26.2.

EXAMPLE 7

Preparation of
1,3-Bis(1H-1,2,4-triazol-1-yl)-2-(4-fluorophenyl)-butan-2-ol

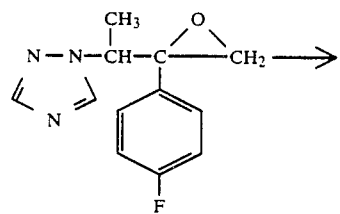

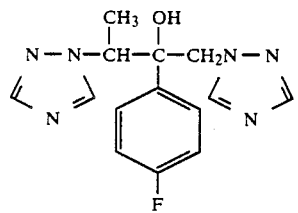

To a solution of 2-(4-fluorophenyl)-2-[1-(1H-1,2,4-triazol-1-yl)ethyl]oxirane (0.5 g, 2.1 mMole) in dimethylformamide (30 ml) was added 1,2,4-triazole (0.29 g, 4.2 mMole) and anhydrous potassium carbonate (0.29 g, 2.1 mMole). Heating, with stirring, was carried out for three hours at 85°. The solvent was evaporated, water (65 ml) was added, and the mixture was then extracted with methylene chloride (3×20 ml). The combined organic extracts were washed with water (3×10 ml), dried over anhydrous magnesium sulphate and evaporated to a gum, (1.1 g). Purification of the gum was carried out using a flash column of Merck "Kieselgel 60" (Trademark) 230–400 mesh silica eluting with methylene chloride containing gradually increasing amounts of methanol (from 5 to 10%). The appropriate fractions, on evaporation, gave the title compound, 318 mg; m.p. 103°–106° (49.1% yield).

Analysis %: Found: C,55.3; H,5.0; N,27.8. Calculated for $C_{14}H_{15}FN_6O$: C,55.6; H,5.0; N,27.7.

N.m.r. and mass spectral data for the product were consistent with the stated structure.

EXAMPLE 8

Preparation of
1,3-bis(1H-1,2,4-triazol-1-yl)-2-(4-fluorophenyl)-3-methylbutan-2-ol

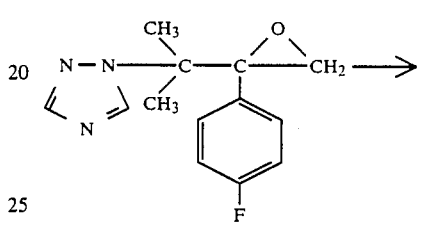

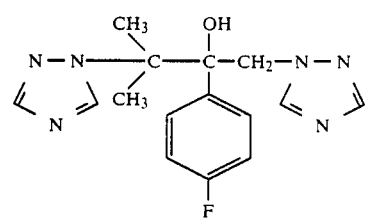

To a solution of 2-(4-fluorophenyl)-2-[2-(1H-1,2,4-triazol-1-yl)prop-2-yl]oxirane (1.0 g, 4.0 mMole) in dimethylformamide (50 ml) were added 1,2,4-triazole (0.56 g., 8.0 mMole) and anhydrous potassium carbonate (0.56 g, 4.0 mMole). Heating at 80°, with stirring, was carried out for 19 hours. The solvent was then evaporated, water (75 ml) was added, and the mixture was extracted with methylene chloride (3×50 ml.). The combined organic extracts were washed with water (3×30 ml), dried over anhydrous magnesium sulphate, and evaporated to an impure gum (1.15 g). Purification of the gum was carried out using a flash column of Merck "Kieselgel 60" (Trademark) 230–400 mesh silica eluting with methylene chloride and 5% methanol in methylene chloride. The appropriate fractions on evaporation gave a solid which was recrystallised from diisopropylether and isopropyl alcohol giving the title compound, 0.4 g., m.p. 156°–158° (31.9% yield).

Analysis %: Found: C,56.9; H,5.4; N,26.6. Calculated for $C_{15}H_{17}FN_6O$: C,57.1; H,5.3; N,26.4.

N.m.r. and mass spectral data for the product were consistent with the stated structure.

EXAMPLES 9 AND 10

The following compounds were prepared similarly to the previous Example from appropriate starting materials:-

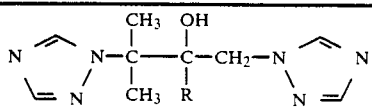

| Example No. | R | m.p. (°C.) | Analysis % (Theoretical in brackets) | | |
|---|---|---|---|---|---|
| | | | C | H | N |
| 9 | (5-chloropyridin-2-yl) | 153-5 | 41.3 (41.35 | 4.4 4.5 | 23.7 24.1) |
| 10 | (2,4-dichlorophenyl) | 156-8 | 48.9 (49.0 | 4.5 4.4 | 22.5 22.9) |

The following Preparations, in which all temperatures are in °C., illustrate the preparation of certain starting materials:

PREPARATION 1

(A) 2',4'-Difluoro-2-methyl-2-(1H-1,2,4-triazol-1-yl)propiophenone

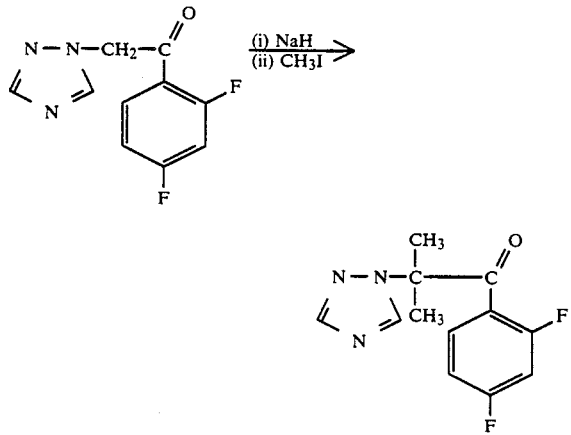

A stirred solution of 2',4'-difluoro-2-(1H-1,2,4-triazol-1-yl)acetophenone (3.7 g, 16.6 m.Mole) in tetrahydrofuran (70 ml) was cooled to 5°, when sodium hydride as a 50% dispersion in oil (1.58 g of said dispersion, which contains 33.2 m.Mole of sodium hydride) was added. Thirty minutes later methyl iodide (5.2 g, 36.5 m.Mole) was added over a five minute period. Stirring was continued for 20 hours at room temperature.

The mixture was then poured into ice-water (150 ml) and extracted with ethyl acetate (3×50 ml). The organic extracts were combined, washed with water (3×20 ml), and dried over anhydrous magnesium sulphate. Evaporation gave an impure solid, weight 4.6 g. Purification was carried out by flash column chromatography under slight pressure (2 p.s.i.) on a Merck "Kieselgel 60" 230-400 mesh silica column, eluting with ether.

The appropriate fractions, on evaporation, gave a solid which was recrystallised from cyclohexane/n-pentane giving the pure title compound, 1.5 g, m.p. 45°-47° (36.3% yield).

Analysis %; Calculated for $C_{12}H_{11}F_2N_3O$: C,57.4; H,4.4; N,16.7. Found: C,57.6; H,4.1; N,16.4.

N.m.r., i.r. and mass spectral data for the product were consistent with the stated structure.

(B) 2-(2,4-Difluorophenyl)-2-[2-(1H-1,2,4-triazol-1-yl)prop-2-yl]oxirane

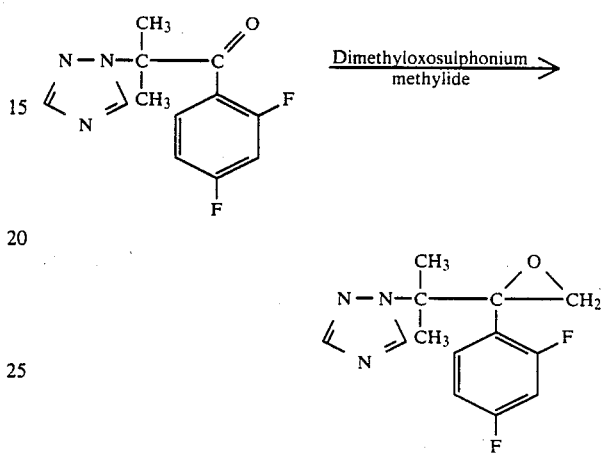

To 2',4'-difluoro-2-methyl-2-(1H-1,2,4-triazol-1-yl)propiophenone (1.45 g, 5.8 m.Mole), trimethylsulphoxonium iodide (2.10 g, 9.6 m.Mole) and cetrimide (0.16 g) were added 1,1,1-trichloroethane (50 ml) and 20% aqueous sodium hydroxide (50 ml). Heating at reflux was carried out for 3 hours with vigorous stirring. The organic layer was separated and washed with water (3×30 ml), dried over anhydrous magnesium sulphate, followed by evaporation to a gum, weight 2.25 g. Purification was by a 15 g Merck "Kieselgel 60" 230-400 mesh silica flash chromatography column eluting with n-pentane containing gradually increasing amounts of methylene chloride (from 0 to 50%) under slight pressure (2 p.s.i.). The appropriate fractions on evaporation gave a solid which was recrystallised from cyclohexane/n-pentane giving the title compound, 0.52 g, m.p. 76°-78° (33.8% yield).

Analysis %: Calculated for $C_{13}H_{13}F_2N_3O$: C,58.8; H,4.9; N,15.8. Found: C,58.9; H,4.9; N,15.8.

N.m.r. and mass spectral data for the product were consistent with the stated structure.

PREPARATION 2

(A) 2',4'-Difluoro-2-(1H-1,2,4-triazol-1-yl)propiophenone hydrochloride

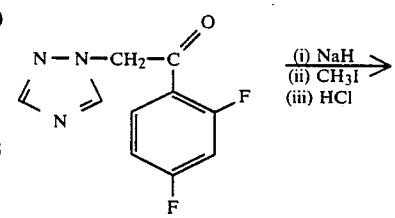

-continued

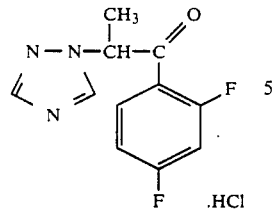

A stirred solution of 2′,4′-difluoro-2-(1H-1,2,4-triazol-1-yl)acetophenone (4 g, 17.9 m.Mole) in tetrahydrofuran (75 ml) was cooled to 5°, when sodium hydride as a 50% dispersion in oil (0.86 g of said dispersion, which contains 17.9 m.Mole of a sodium hydride) was added. Twenty minutes later methyl iodide (2.8 g, 19.7 m.Mole) was added over a five minute period. Stirring was continued for 19 hours at room temperature. The mixture was then poured into ice-water (100 ml) and extracted with methylene chloride (3×30 ml). The combined organic extracts were washed with water (3×40 ml) and dried over anhydrous magnesium sulphate. On evaporation an oil was obtained, weight 4.7 g. Purification was carried out by flash column chromatography under slight pressure (2 p.s.i.) on a Merck "Kieselgel 60" 230–400 mesh silica column, eluting with ether. The appropriate combined fractions were reduced in volume (to 50 ml) by evaporation and then treated with gaseous hydrogen chloride. The resulting hydrochloride salt was filtered off and recrystallised from isopropanol, giving the pure title compound, 1.66 g, m.p. 147°–150°, as fine crystals (33.9% yield).

Analysis %: Calculated for $C_{11}H_9F_2N_3O \cdot HCl$: C,48.3; H,3.7; N,15.4. Found: C,48.1; H,3.5; N,15.7.

N.m.r., i.r. and mass spectral data for the product were consistant with the stated structure.

-continued

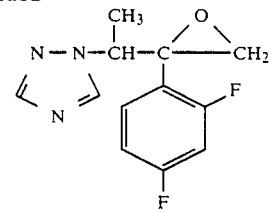

To 2′,4′-difluoro-2-(1H-1,2,4-triazol-1-yl)propiophenone hydrochloride (1.36 g, 5.0 m.Mole), trimethylsulphoxonium iodide (1.32 g, 6.0 m.Mole) and cetrimide (0.15 g) were added 1,1,1-trichloroethane (25 ml) and 20% aqueous sodium hydroxide (25 ml). Heating at reflux was carried out for 1½ hours with vigorous stirring. The separated organic phase was washed with water (3×10 ml) and dried over anhydrous magnesium sulphate. On evaporation a gum was obtained, weight 1.6 g. Purification was by flash column chromatography under slight pressure (2 p.s.i.) on Merck "Kieselgel 60" 230–400 mesh silica eluting with ether containing gradually increasing amount of ethanol (from 1 to 5%). The appropriate fractions gave on evaporation a solid which was recrystallised from cyclohexane giving the title compound, 0.6 g, m.p. 85°–87°, (39.5% yield).

Analysis %: Calculated for $C_{12}H_{11}F_2N_3O$: C,57.4; H,4.4; N,16.7 Found: C,57.3; H,4.4; N,16.8.

N.m.r., i.r. and mass spectral data for the product were consistent with the stated structure.

PREPARATION 3

(A) 2-[2-(1H-1,2,4-Triazol-1-yl)acetyl]-5-chloropyridine

This intermediate was prepared conventionally according to the following scheme:

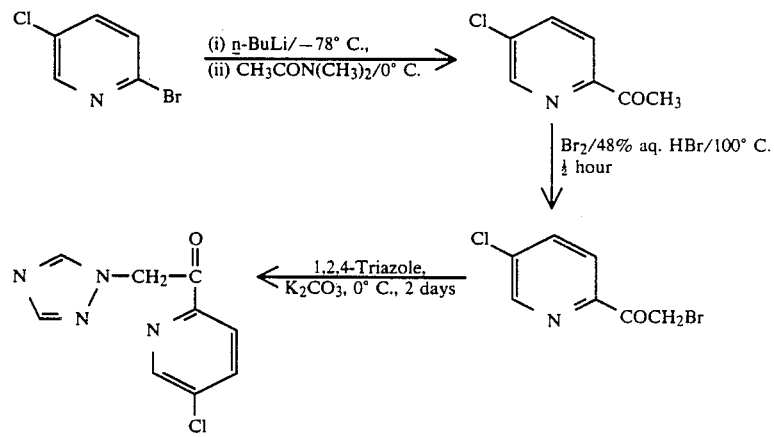

(B) 2-(2,4-Difluorophenyl)-2-[1H-1,2,4-triazol-1-yl)ethyl]oxirane

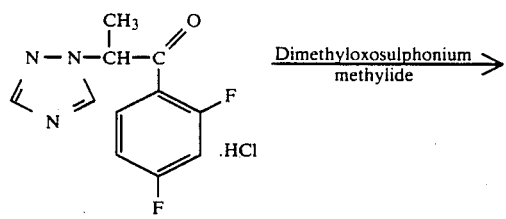

(B) 2-[2-(1H-1,2,4-Triazol-1-yl)propionyl]-5-chloropyridine

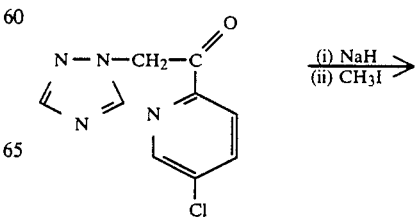

-continued

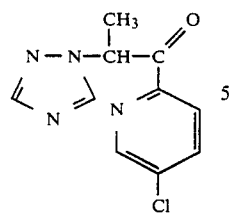

A stirred solution of 2-[2-(1H-1,2,4-triazol-1-yl)acetyl]-5-chloropyridine (1 g, 4.5 mMole) in tetrahydrofuran (60 ml) was cooled to 5°, when sodium hydride as a 50% dispersion in oil (0.32 g of said dispersion, which contains 6.7 m.Mole of sodium hydride) was added. Forty minutes later methyl iodide (0.7 g, 4.9 m.Mole) was added over a five minute period. Stirring was continued for 20 hours at room temperature. The reaction mixture was then poured into ice-water (100 ml) and extracted with ethyl acetate (3×30 ml). The combined organic extracts were washed with water (3×30 ml), dried over anhydrous magnesium sulphate, and evaporated to an oil (1.2 g).

Purification was carried out by flash column chromatography under slight pressure (2 p.s.i.) on a Merck "Kieselgel 60" 230–400 mesh silica column, eluting with ether. The appropriate fractions on evaporation gave the title compound as a crystalline solid, 0.22 g, m.p. 99°–101° (20.7% yield).

Analysis %: Calculated for C$_{10}$H$_9$ClN$_4$O: C,50.8; H,3.8; N,23.7. Found: C,50.7; H,3.8; N,23.8.

N.m.r. and mass spectral data for the product were consistent with the stated structure.

(C) 2-(5-Chloropyrid-2-yl)-2-[1-(1H-1,2,4-triazol-1-yl)ethyl]oxirane

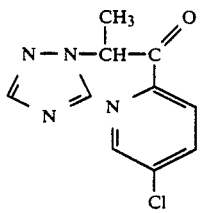

Dimethyloxosulphonium methylide →

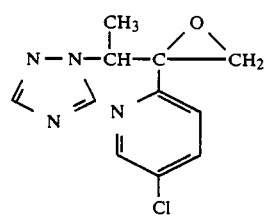

To 2-[2-(1H-1,2,4-triazol-1-yl)propionyl]-5-chloropyridine (0.17 g, 0.71 m.Mole), trimethylsulphoxonium iodide (0.19 g, 0.85 m.Mole) and cetrimide (0.02 g), were added 1,1,1-trichloroethane (10 ml) and 20% aqueous sodium hydroxide (10 ml). Heating at reflux, with vigorous stirring, was carried out for 1½ hours. The separated organic phase was washed with water (3×5 ml) and dried over anhydrous magnesium sulphate. On evaporation a gum was obtained (0.13 g).

Purification was by flash column chromatography under slight pressure (2 p.s.i.) on Merck "Kieselgel 60" 230–400 mesh silica eluting with ether containing gradually increasing amounts of ethanol (from 1 to 5%). The appropriate fractions gave, on evaporation, the title compound as a fine crystalline solid, 0.07 g, m.p. 101°–104° (39.5% yield). N.m.r. and i.r. were consistent with the stated structure.

PREPARATION 4

(A) Preparation of 4'-fluoro-2-(1H-1,2,4-triazol-1-yl)acetophenone

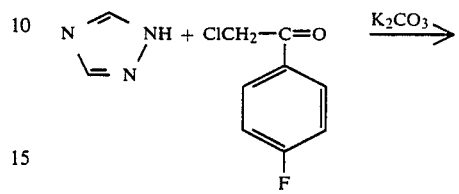

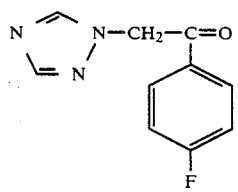

Alkylation of 1,2,4-triazole (14 g) with 2-chloro-4'-fluoroacetophenone (8.6 g) in the presence of potassium carbonate (20 g) in dry acetone (150 ml) yielded the title compound, which was crystallised from water, m.p. 134°, (5.4 g).

Analysis %: Found: C,58.4; H,3.9; N,20.5. Calculated for C$_{10}$H$_8$FN$_3$O: C,58.5; H,3.9; N,20.5.

(B) Preparation 4'-fluoro-2-(1H-1,2,4-triazol-1-yl)propiophenone hydrochloride

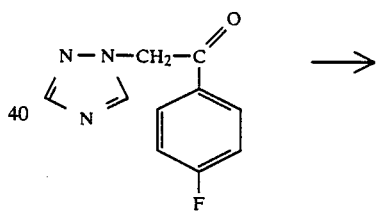

→

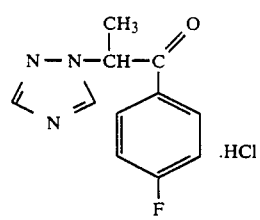

To a stirred solution of 4'-fluoro-2-(1H-1,2,4-triazol-1-yl)acetophenone (2.05 g., 10 mMole) in tetrahydrofuran (40 ml) at 5°, was added sodium hydride as a 50% dispersion in oil (0.53 g. of dispersion containing 11 mMole of sodium hydride). Fifteen minutes later methyl iodide (1.56 g, 11 mMole) was added over a five minute period. Stirring was continued for 19 hours at room temperature. The mixture was then poured into saturated saline solution (100 ml) and extracted with ethyl acetate (3×40 ml). The organic extracts were combined, washed with water (3×30 ml) and dried over anhydrous magnesium sulphate. Evaporation gave an impure oil (2.2 g). Purification of the oil was carried out by flash column chromatography under slight pressure (2 p.s.i.) on a Merck "Kieselgel 60" (Trademark)

230–400 mesh silica-packed column, eluting with ether. The appropriate fractions, on evaporation, gave a gum which was dissolved in ether (35 ml) and treated with gaseous hydrogen chloride. The resulting hydrochloride salt was filtered off and recrystallised from isopropanol to give the pure title compound, 1.38 g, m.p. 141°–145° (53.9% yield).

Analysis %: Found: C,51.7; H,4.3; N,16.4. Calculated for $C_{11}H_{10}FN_3O \cdot HCl$: C,51.5; H,4.3; N, 16.3.

N.m.r. and mass spectral data for the product were consistent with the stated structure. (C) Preparation 2-(4-Fluorophenyl)-2-[1-(1H-1,2,4-triazol-1-yl)ethyl]oxirane

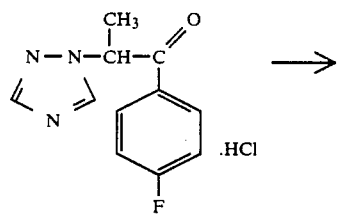

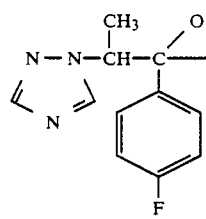

To 4'-fluoro-2-(1H-1,2,4-triazol-1-yl) propiophenone hydrochloride (1.1 g, 4.3 mMole) trimethyl sulphoxonium (1.6 g, 7.7 mMole) and cetrimide (150 mg) were were added 1,1,1-trichloroethane (25 ml) and 20% aqueous sodium hydroxide (25 ml). Heating at reflux, with vigorous stirring, was carried out for 2 hours. The separated organic phase was washed with water (3×10 ml) and dried over anhydrous magnesium sulphate. On evaporation the title compound was obtained as a solid, 1.0 g; (99% yield). N.m.r. and i.r. spectral data for the product were consistent with the stated structure.

EXAMPLE 5

(A) Preparation of 4'-fluoro-2-methyl-2-(1H-1,2,4-triazol-1-yl)propiophenone

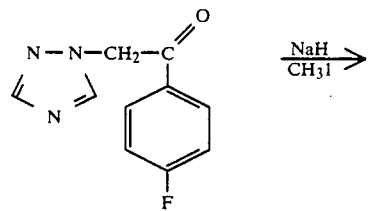

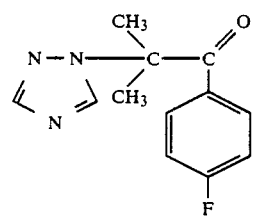

To a stirred solution of 4'-fluoro-2-(1H-1,2,4-triazol-1-yl)acetophenone (2.05 g; 10 mMole) in tetrahydrofuran (40 ml) at 5°, was added sodium hydride as a 50% dispersion in oil (1.06 g of said dispersion which contains 22 mMole of sodium hydride). Fifteen minutes later methyl iodide (2.84 g, 20 mMole) was added over a three minute period. Stirring was continued for 19 hours at room temperature. The mixture was then poured into saturated saline solution (100 ml) and extracted with ethyl acetate (3×40 ml). The organic extracts were combined, washed with water (3×30 ml) and dried over anhydrous magnesium sulphate. Evaporation gave an impure solid (2.0 g). Purification of the solid was carried out by flash column chromatography under slight pressure (2 p.s.i.) on an Merck "Kieselgel 60" (Trademark) 230–400 mesh silica-packed column eluting with ether. The appropriate fractions, on evaporation, gave a solid which was recrystallised from cyclohexane to give the pure title compound, 0.76 g; m.p. 111°–112° (32.6% yield).

Analysis %: Found: C,61.8; H,5.2; N,18.0 Calculated for $C_{12}H_{12}FN_3O$: C,61.8; H,5.2; N,17.8.

N.m.r. and mass spectral data for the product were consistent with the stated structure.

(B) Preparation of 2-(4-fluorophenyl-2-[(2-(1H-1,2,4-triazol-1-yl)prop-2-yl]oxirane

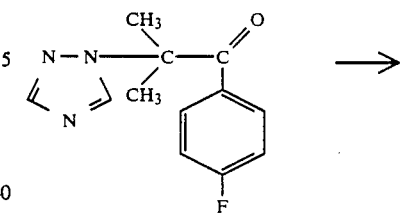

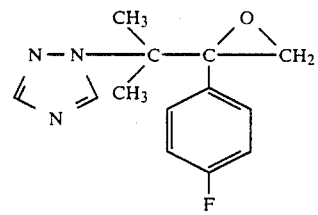

To 4'-fluoro-2-methyl-2-(1H-1,2,4-triazol-1-yl)propiophenone (0.75 g, 3.2 mMole), trimethylsulphoxonium iodide (1.16 g, 5.3 mMole) and cetrimide (100 mg) were added 1,1,1-trichloroethane (30 ml) and 20% aqueous sodium hydroxide (30 ml). Heating at reflux was carried out for 5 hours with vigorous stirring. The organic layer was then separated, washed with water (3×20 ml), dried over anhydrous magnesium sulphate, and evaporated to yield the title compound as a solid, 0.7 g; (88.3% yield). N.m.r. and i.r. spectral data for the product were consistent with the stated structure.

The following ketones were prepared similarly to part (A) above from appropriate starting materials:

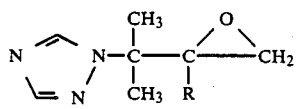

| R | m.p. (°C.) | Analysis % Theoretical in brackets | | |
|---|---|---|---|---|
| | | C | H | N |
| ![pyridine-Cl] | 91–3 | 52.5 (52.7 | 4.3 4.4 | 22.6 22.35) |
| ![dichlorophenyl].HCl | 117–120 | 45.0 (45.0 | 3.8 3.7 | 13.1 13.3) |

The following oxiranes were prepared similarly to part (B) from the above ketones, but were not characterised in detail:

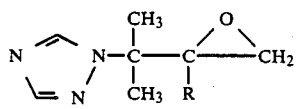

PREPARATION 6

(A) Preparation of 4'-chloro-2-(1H-1,2,4-triazol-1-yl)propiophenone

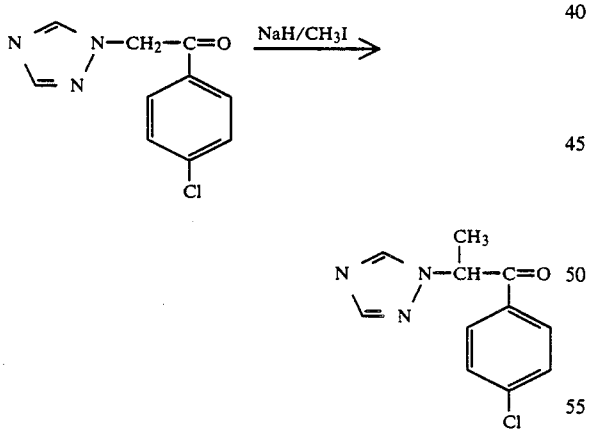

Alkylation of 4'-chloro-2-(1H-1,2,4-triazol-1-yl)acetophenone (3 g.) (see DT-OS 2431407) with methyl iodide (2.05 g). in the presence of sodium hydride (as a 60 weight per cent dispersion in oil, total weight of dispersion 550 mg.) in tetrahydrofuran (50 ml.) yielded the title compound, m.p. 85°, 2.4 g., characterised spectroscopically.

Mass spectral data: m/e 234 (M+), 139, 111. Calculated for $C_{11}H_{10}ClN_3O$, M+ =234.

(B) Preparation of 2-(4-chlorophenyl)-2-[1-(1H-1,2,4-triazol-1-yl)ethyl]oxirane methanesulphonate salt

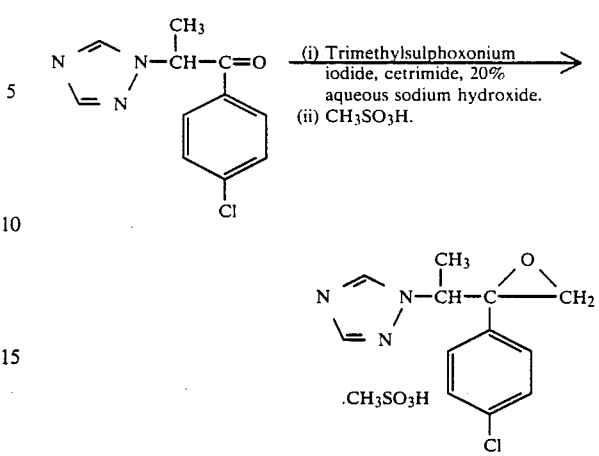

The title compound was prepared similarly to Preparation 5(B), starting from 4'-chloro-2-(1H-1,2,4-triazol-1-yl)propiophenone (2.35 g.), trimethylsulphoxonium iodide (2.72 g.), cetrimide (150 mg.), 1,1,1-trichloroethane (30 ml.) and 20% aqueous sodium hydroxide (25 ml.). The residue left after evaporation of the organic layer was dissolved in acetone (25 ml) and treated with methanesulphonic acid (0.8 g.) to precipitate the title methanesulphonate salt, 2.05 g., m.p. 154°–155°, characterised spectroscopically.

Mass spectral data: m/e 249 (M+), 233, 180, 153, 125, 96, 82; Calculated for $C_{12}H_{12}ClN_3O$, $M^{\oplus}=249$.

The PD$_{50}$ values (oral) for the compounds of the formula (I) vs. *C. albicans* in mice obtained by the test method described in the text are as follows:

| Compound | PD$_{50}$ (mg./kg.) |
|---|---|
| Product of Example 1 | 0.4 |
| Product of Example 2 | 0.1 |
| Product of Example 3 | 0.2 |
| Product of Example 4 | 0.2 |
| Product of Example 5 (diastereomer pair 1) | 0.1 |
| Product of Example 5 (diastereomer pair 2) | 0.3 |
| Product of Example 6 (diastereomer pair 2) | 0.5 |
| Product of Example 7 | 0.1 |
| Product of Example 8 | 0.3 |
| Product of Example 9 | 0.5 |
| Product of Example 10 | 1.6 |

In tests for activity against systemic aspergillosis in mice, mice are infected with a Pfizer-maintained strain of *Aspergillus flavus* by i.v. injection via the tail vein. Untreated (control) mice normally die within 5 to 10 days of infection with *A. flavus*. Each test compound is administered to a group of infected mice at an oral dose level of 20 mg./kg 1 hour and 4 hours after infection, and then twice daily for the next 4 days. The increase in mean survival time (MST) of the treated mice compared with that of a control group of mice infected with the same strain at the same time, is then determined.

The compounds of the formula (I) have been found to be unexpectedly active against the important strain *A. flavus*, and the results set out below compare these compounds against their analogues having "—CH$_2$—" (see GB 2078719A) as compared to $$-\overset{R^1}{\underset{CH_3}{C}}-$$

in the chain.

$$\underset{N}{\overset{N}{\diagdown}}N-CH_2-\underset{R}{\overset{OH}{\underset{|}{C}}}-\underset{R^2}{\overset{R^1}{\underset{|}{C}}}-N\underset{N}{\diagdown}\overset{N}{\diagup}$$

| R | $R^1$ | $R^2$ | Increase in MST (days) |
|---|---|---|---|
| 2,4-difluorophenyl (product of Example 2) | H | $CH_3$ | +20 |
| 2,4-difluorophenyl (product of Example 1) | $CH_3$ | $CH_3$ | +13 |
| 2,4-difluorophenyl | H | H | +4.5 |
| 5-chloropyrid-2-yl (Product of Example 3) | H | $CH_3$ | +7 |
| 5-chloropyrid-2-yl | H | H | +3 |
| 4-fluorophenyl (Product of Example 7) | H | $CH_3$ | +5.4 |
| 4-fluorophenyl (Product of Example 8) | $CH_3$ | $CH_3$ | +9.6 |
| 4-fluorophenyl | H | H | +1 |
| 4-chlorophenyl (Diastereomer 1 from Example 5) | H | $CH_3$ | +18.6 |
| 4-chlorophenyl (Product of Example 4) | $CH_3$ | $CH_3$ | +15 |
| 4-chlorophenyl | H | H | +2.4 |

I claim:
1. The compound of the formula

$$\underset{N}{\overset{N}{\diagdown}}N-CH_2-\underset{R}{\overset{OH}{\underset{|}{C}}}-\underset{CH_3}{\overset{R^1}{\underset{|}{C}}}-N\underset{N}{\diagdown}\overset{N}{\diagup}$$

or an O-($C_{2-4}$ alkanoyl) or O-benzoyl ester thereof; or an O-($C_{1-4}$ alkyl), $C_{2-4}$ alkenyl, phenyl-($C_{1-4}$ alkyl) or phenyl ether thereof; or a pharmaceutically or agriculturally acceptable salt thereof;
wherein R is 5-chloropyrid-2-yl and $R^1$ is H.

2. A method of treating a plant or seed having a fungal infection, which comprises contacting said plant or seed, or the locus of said plant, with an antifungally effective amount of a compound of the formula $$\underset{N}{\overset{N}{\diagdown}}N-CH_2-\underset{R}{\overset{OH}{\underset{|}{C}}}-\underset{CH_3}{\overset{R^1}{\underset{|}{C}}}-N\underset{N}{\diagdown}\overset{N}{\diagup} \qquad (I)$$

or an O-($C_{2-4}$ alkanoyl) or O-benzoyl ester thereof; or an O-($C_{1-4}$ alkyl), $C_{2-4}$ alkenyl, phenyl-($C_{1-4}$ alkyl) or phenyl ether thereof; or a pharmaceutically or agriculturally acceptable salt thereof;
wherein R is 5-chloropyrid-2-yl or phenyl substituted by 1 to 2 substituents selected from F and Cl; and $R^1$ is H or $CH_3$.

* * * * *